United States Patent
Tornier et al.

(10) Patent No.: US 8,246,653 B2
(45) Date of Patent: Aug. 21, 2012

(54) DEVICE FOR THE LATERAL STABILIZATION OF THE SPINE

(75) Inventors: Alain Tornier, Saint Ismier (FR); Irene Ferrari-Gosset, Saint Vincent de Mercuze (FR)

(73) Assignee: Clariance, Dainville (FR)

( * ) Notice: Subject to any disclaimer, the term of this patent is extended or adjusted under 35 U.S.C. 154(b) by 919 days.

(21) Appl. No.: 11/634,375

(22) Filed: Dec. 6, 2006

(65) Prior Publication Data
US 2007/0162003 A1  Jul. 12, 2007

Related U.S. Application Data

(60) Provisional application No. 60/748,601, filed on Dec. 9, 2005.

(30) Foreign Application Priority Data

Dec. 7, 2005  (FR) ...................................... 05 12427

(51) Int. Cl.
*A61B 17/70* (2006.01)
(52) U.S. Cl. .................................................... 606/246
(58) Field of Classification Search .................. 606/246, 606/247, 257, 279; 623/17.11–17.16; 403/13, 403/14, 80, 112
See application file for complete search history.

(56) References Cited

U.S. PATENT DOCUMENTS

| | | | |
|---|---|---|---|
| 5,423,816 A | 6/1995 | Lin | |
| 6,296,644 B1 | 10/2001 | Saurat | |
| 2003/0004572 A1* | 1/2003 | Goble et al. | 623/17.11 |
| 2004/0049272 A1* | 3/2004 | Reiley | 623/17.11 |
| 2005/0113927 A1 | 5/2005 | Malek | |
| 2005/0131537 A1* | 6/2005 | Hoy et al. | 606/61 |
| 2006/0084987 A1* | 4/2006 | Kim | 606/61 |

FOREIGN PATENT DOCUMENTS

| | | |
|---|---|---|
| DE | 29814320 | 11/1998 |
| JP | 102777070 | 10/1998 |

* cited by examiner

*Primary Examiner* — Eduardo C Robert
*Assistant Examiner* — Steven Cotroneo
(74) *Attorney, Agent, or Firm* — Young & Thompson

(57) ABSTRACT

The device (9) comprises vertebral elements (10, 20, 10', 20') adapted to be fixed to the same lateral side of the bodies of at least two adjacent vertebrae (1, 2), the elements being associated in pairs that are provided to be associated with the left and right sides of the vertebrae. In order to guide the vertebrae effectively and stably, in order, in use, to reproduce an articulating intervertebral joint, the two elements of each pair delimit respective surfaces (15, 25, 15', 25') for the relative guiding of those elements, which surfaces are adapted, when the elements are implanted on their corresponding vertebra, to extend generally along the same lateral side of the body of the vertebrae and to rest and slide one against the other in such a manner that the surfaces define a center of rotation (C) about which the two elements are able to turn one relative to the other.

23 Claims, 3 Drawing Sheets

DEVICE FOR THE LATERAL STABILIZATION OF THE SPINE

BACKGROUND OF THE INVENTION

1. Field of the Invention

The present invention relates to a device for the lateral stabilization of the spine, which device is to be implanted along the vertebral column in the region of one or both of its left and right lateral sides, in order to stabilize at least two vertebrae one relative to the other. Such stabilization is desirable especially within the context of the treatment of degenerative or traumatized spine. The invention relates more particularly to the treatment of the dorsolumbar spine, but is likewise applicable to the treatment of the cervical spine.

2. Brief Description of the Related Art

For the treatment of an intervertebral instability, a first known possibility comprises fusing two adjacent vertebrae, which amounts to depriving those two vertebrae of their relative freedom of movement. Totally rigid assemblies are implanted for that purpose in a fixed manner along the spine in order permanently to block the articulating joint between the two vertebrae to be fused. U.S. Pat. No. 6,296,644 accordingly proposes a vertebral assembly constituted by a plurality of vertebral elements which are to be fixed to the same number of vertebrae and which are connected in pairs by "lockable" joints: when the assembly is being fitted, the joints are movable in order to facilitate the relative positioning of the vertebral elements along the spine, and then, when fitting is complete, the joints are fixed permanently by means of rings having shape memory so that, in use, the vertebral elements are completely fixed relative to one another. However, this type of operation of arthrodesis of the vertebrae leads to degeneration of the adjacent disks, on which it is subsequently necessary to operate.

Another known possibility for treatment of the spine comprises operating at an earlier stage than that which involves arthrodesis. A first solution of that type is proposed in DE-U-298 14 320: a plurality of separate vertebral elements, each fixed to adjacent vertebrae, are in use movable relative to one another, while being connected in pairs by rectilinear telescopic joints according to the longitudinal direction of the spine. This movable assembly adapts to a certain development of the kinematic behavior of the spine, for example as it grows, but does not provide actual dynamic stabilization of the vertebrae and accordingly does not prevent, for example, crushing or deformation of the intervertebral disks.

A second solution is proposed in JP-A-10 277070: the posterior sides of two adjacent vertebrae are connected vertically by two pistons, a sleeve of resilient material being inserted between the male part and the female part of each piston. The transverse cross-section of each piston is elliptical, which on the one hand prevents the male and female parts of the piston from being guided in rotation one relative to the other about a vertical axis and on the other hand centres the articulating movements between the male and female parts either in the piston or in a plane that passes through the two pistons, that is to say well behind the vertebrae. The kinematics imposed on the vertebrae is accordingly very different from the normal anatomical behavior of the spine, with considerable risks that the intervertebral disk will be pinched, or even crushed, at least in its anterior portion.

Other solutions aim to implant a lateral device for dynamic stabilization, such as those proposed in U.S. Pat. No. 5,423,816, U.S. Pat. No. 5,704,936 and U.S. Pat. No. 6,616,669. To that end, this type of device comprises, on the one hand, rigid elements that are to be anchored in the bone of the same lateral side of two adjacent vertebrae and, on the other hand, flexible joining elements between the rigid elements. These flexible elements, such as springs or flexible arms, extend laterally along the spine and thus relieve the intervertebral disk by reducing any excess pressure in the region of the articulating surfaces between that disk and the vertebrae. Such devices are more comfortable for the patient because they allow the mobility of the spine to be retained. However, the use of that type of dynamic device is found to be difficult in practice. Dimensioning of the flexibility of the joining elements is difficult because it must be adapted to each patient according to his pathology and morphology and, in the long term, the resilient behavior of those elements changes. If those parameters are poorly controlled, it is not possible to ensure that a kinematics appropriate to the spine is respected, which can lead to poor stabilization of the intervertebral space and to aggravation of the damage that it is desired to treat.

OBJECT OF THE INVENTION

The object of the present invention is to propose a device for the lateral stabilization of the spine that reproduces the anatomical movements of the vertebrae more faithfully, is more effective for stabilizing the vertebrae to be treated and is more reliable over time.

To that end, the invention relates to a device for the lateral stabilization of the spine which is intended, in use, to reproduce an articulating intervertebral joint, comprising at least two vertebral elements which are each adapted to be fixed to the same lateral side of the bodies of at least two adjacent vertebrae, characterized in that the two vertebral elements delimit respective surfaces for the relative guiding of the elements, which surfaces, when the elements are implanted on their corresponding vertebra, are adapted to extend generally along the same lateral side of the body of the vertebrae and to rest and slide one against the other in such a manner that the surfaces define a centre of rotation which is located in the intervertebral disk space separating the two adjacent vertebrae and about which the two elements are able to turn one relative to the other.

The fact that the two vertebral elements of the device according to the invention are guided one relative to the other by the guide surfaces, which are delimited by those elements and cooperate one with the other by sliding bearing, makes it possible to confer on the device precise kinematic behavior that is stable over time. The imposed kinematics, namely a rotary movement between the two vertebral elements about the centre of rotation positioned, in a predetermined manner, in the disk space, ensures that the intervertebral articulating movements induced when the spine is stressed are guided effectively in order to be quasi-identical with, or at least as similar as possible to, normal anatomical behavior of the spine. In that manner, the cooperation of the lateral guide surfaces can allow a satisfactory intervertebral spacing to be retained, while maintaining a predetermined vertical spacing of the vertebrae. The device according to the invention accordingly bears the majority, or even the totality, of the stresses applied to the intervertebral disk, which remains mobile. Furthermore, implantation of the device according to the invention is found to be particularly simple: the mobilities particular to the device reside substantially, or even exclusively, in the region of the guide surfaces carried by the two vertebral elements, the anchoring positions, preferably lateral, of which in the two vertebrae to be treated are chosen and fixed by the surgeon. Since those guide surfaces extend laterally relative to the spine, surgical actions are concentrated in lateral zones relative to the spine.

According to other advantageous features of this device, taken in isolation or according to all the technically possible combinations:

the guide surfaces are convex and concave, respectively, while being substantially mutually complementary;

the centre of rotation is located in or in the vicinity of the intervertebral disk space separating the two vertebrae equipped with the vertebral elements;

each guide surface corresponds substantially to a portion of a sphere, the centre of which corresponds to the centre of rotation;

the guide surfaces define a permanent centre of rotation when the vertebrae equipped with the two vertebral elements are displaced one relative to the other;

the guide surfaces define a plurality of instantaneous centres of rotation when the vertebrae equipped with the two vertebral elements are displaced one relative to the other;

the device includes means for limiting the amplitude of the relative rotary movements between the vertebral elements;

the limiting means comprise, on the one hand, a pin which is fast with one of the vertebral elements and projects from the guide surface carried by that element in the direction towards the guide surface carried by the other element, and, on the other hand, an aperture adapted to receive the pin with clearance, the aperture being formed by the other vertebral element and opening at the guide surface carried by the latter;

the part of each vertebral element on which the corresponding guide surface is delimited is generally in the form of a truncated cup, which is centred substantially on the centre of rotation;

each part in cup form has a concavity turned towards that lateral side of the bodies of the vertebrae along which the guide surfaces extend;

the device has four vertebral elements associated in pairs that are provided to be associated with the left and right sides of the two vertebrae;

the centres of rotation associated with each pair of vertebral elements are substantially coincident.

BRIEF DESCRIPTION OF DRAWINGS

The invention will better be understood upon reading the following description, which is given solely by way of example and with reference to the drawings, in which.

DESCRIPTION OF THE PREFERRED EMBODIMENT

Figure 1:
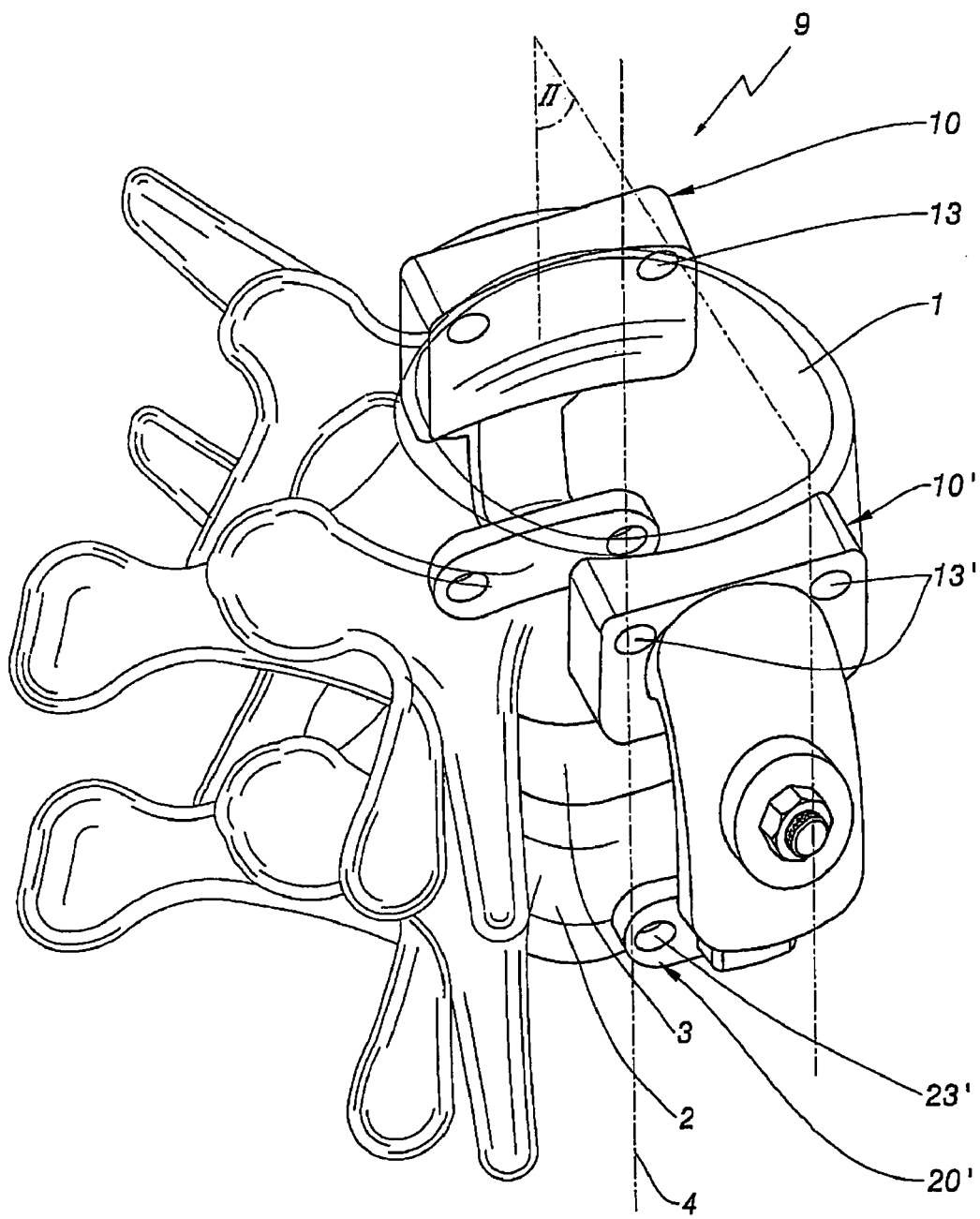
FIG. 1 is a diagrammatic view, in perspective, of two adjacent vertebrae equipped with a lateral stabilization device according to the invention, the vertebrae and the device being viewed from the rear, in a manner offset relative to the sagittal plane of the spine and according to a downwardly directed observation direction.
Figure 2:
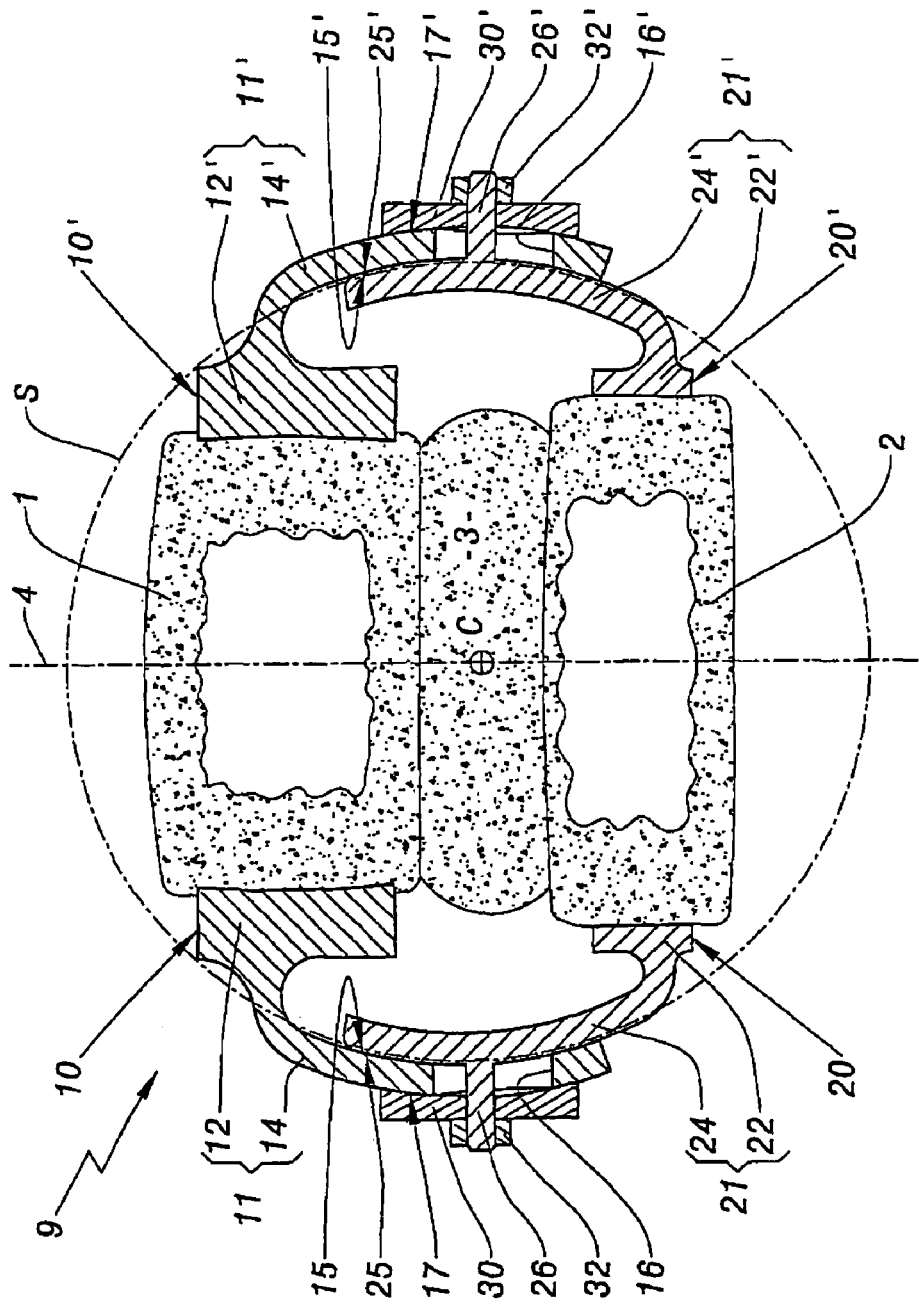
FIG. 2 is a diagrammatic section according to plane II of FIG. 1.

FIGS. 1 and 2 show, in diagrammatic form, two adjacent vertebrae 1 and 2 of a lumbar spine of a human being, which vertebrae are separated by an intervertebral disk 3 according to the longitudinal direction 4 of the spine. For convenience, the remainder of the description is oriented relative to the vertebrae in their anatomical position, that is to say the terms "posterior" or "rear", "anterior" or "front", "right", "left", "upper", "lower", etc. are to be understood relative to the spine of the patient standing upright. Likewise, the term "sagittal" corresponds to a direction in the anteroposterior direction, vertically on the median line of the spine, while the term "medial" corresponds to a direction substantially perpendicular to the sagittal plane of the spine, directed towards the spine, the term "lateral" corresponding to the opposite direction.

Figure 3:
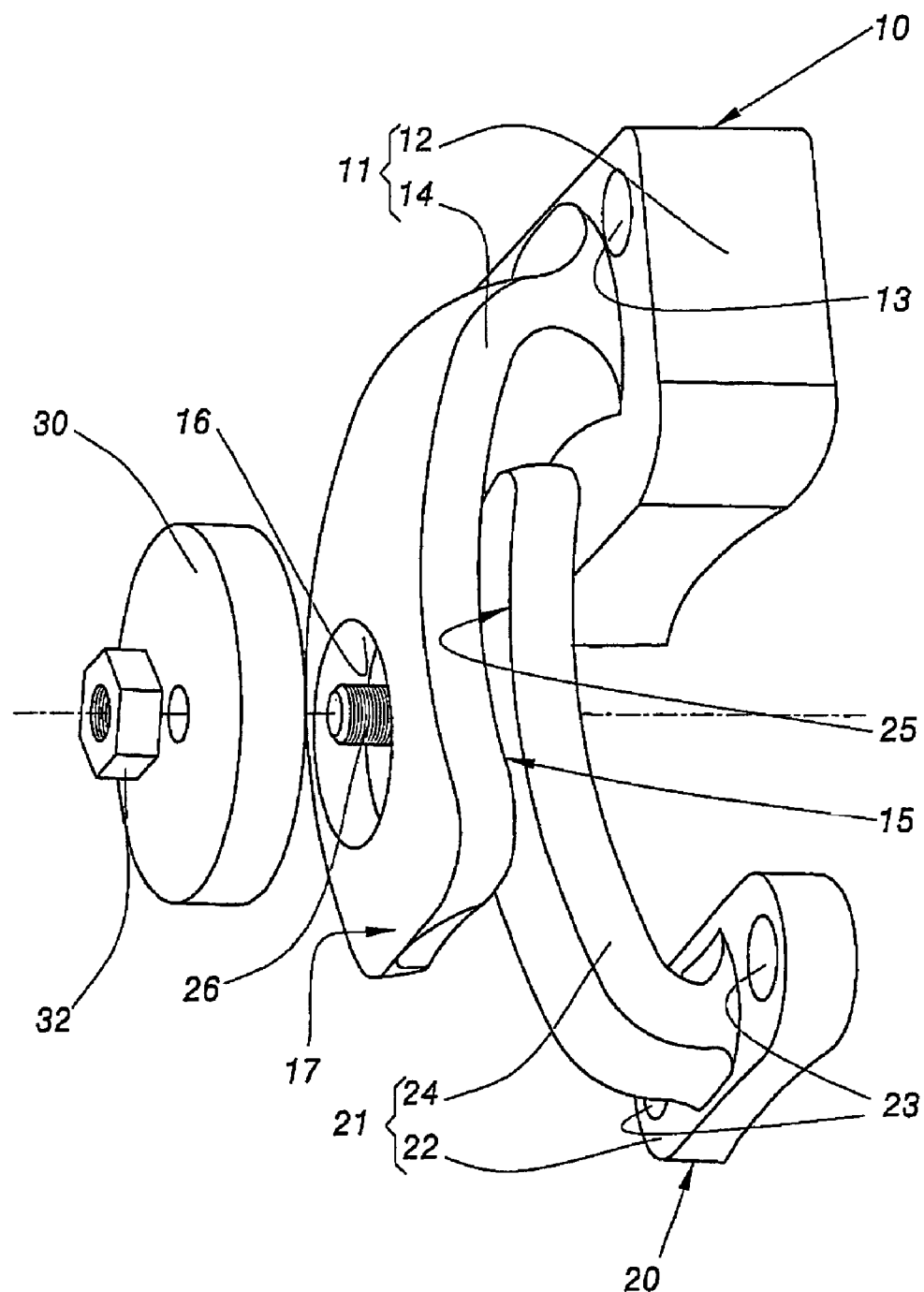
FIG. 3 is an exploded view, in perspective, of a lateral part of the device of the preceding Figures.

FIGS. 1 and 3 show a device 9 for the dynamic stabilization of the vertebrae 1 and 2, which device is implanted on the left and right sides of the vertebrae in order to reproduce the articulating joint between the vertebrae while providing satisfactory intervertebral spacing. The device comprises four vertebral elements which are associated in pairs on the left and right sides of the vertebrae. The left-hand pair includes an upper vertebral element 10 implanted in the region of the vertebra 1, and a lower vertebral element 20 implanted in the region of the vertebra 2. In a symmetrical manner relative to the sagittal plane of the spine, the direction of which in the plane of FIG. 2 corresponds to the longitudinal direction 4 of the spine, the right-hand pair includes two vertebral elements 10' and 20' implanted in the region of the vertebrae 1 and 2, respectively. For convenience, only the left-hand vertebral elements will be described in detail hereinbelow, it being understood that the right-hand vertebral elements 10' and 20' have analogous arrangements, which can be deduced by symmetry relative to the sagittal plane of the spine and which bear the same reference numerals as the arrangements of the left-hand elements, but followed by a prime.

Each vertebral element 10, 20 has a rigid body 11, 21 in a single piece, especially made of metal, which is adapted to be fixed to the left side of the vertebra 1, 2. To that end, apertures 13, 23 pass right through the upper part 12 of the body 11 and the lower part 22 of the body 21, according to a mediolateral direction, which apertures 13, 23 are intended to receive screws (not shown) for bone anchoring in the vertebral body of the vertebrae 1 and 2 in order firmly to immobilize the vertebral elements relative to the vertebrae.

The lower part 14 of the element 10 and the upper part 24 of the element 20 are adapted to cooperate with one another when the device 9 is implanted, as shown in FIGS. 1 and 2. Each of those parts 14, 24 is generally in the form of a cup, the concavity of which is turned towards the left side of the bodies of the vertebrae 1 and 2. The anterior and posterior end portions of each of the parts 14 and 24 in cup form are truncated in such a manner that the principal dimension of each part 14 and 24 extends substantially along the left side of the bodies of the vertebrae 1 and 2, that is to say substantially parallel to the longitudinal direction 4 of the spine. In frontal section, as in FIG. 2, that is to say in a substantially vertical cutting plane parallel to a mediolateral direction, the body 11, constituted by the upper and lower parts 12 and 14, which are integral with one another, has a cross-section which is generally in the form of an inverted L, the main limb of which is rounded in a direction facing the spine, while the body 21, which is constituted by the lower and upper parts 22 and 24, which are integral with one another, has a generally L-shaped cross-section, the main limb of which is likewise rounded in a direction facing the spine. The parts 14 and 24 are of such relative sizes that, when the device 9 is implanted, the part 14 covers the part 24 laterally.

More precisely, the lower part 14 of the element 10 delimits, on its medial face, a concave surface 15, while the upper part 24 of the element 20 delimits, on its lateral face, a convex surface 25 which is intended to rest and slide against the concave surface 15. In the example shown in the figures, the surfaces 15 and 25 are substantially mutually complementary and correspond approximately to portions of a sphere S having a centre C, as shown in FIG. 2. In this manner, when the elements 10 and 20 are fixed to the vertebrae 1 and 2, the surfaces 15 and 25 rest against one another in a sliding manner and are movable one relative to the other by rotation about the centre C, in the manner of a ball-and-socket joint of centre C.

In use, when the device 9 is implanted on the vertebrae 1 and 2, the surfaces 15 and 25 cooperate in such a manner as to guide the articulating movements between the vertebrae about the point C. Since that point is advantageously located in the intervertebral disk space in which the disk 3 is lodged, in particular in the central region of that space, the rotary movements imposed by the cooperation of those surfaces are identical with, or at least very similar to, the anatomical intervertebral articulating movements generated when the spine is stressed. The sphere/sphere contact between the surfaces 15 and 25 relates in theory the guiding achieved to that of a ball-and-socket joint of centre C. In practice, on account of the play between those surfaces and on account of the ligamentary environment of the vertebrae 1 and 2, the surfaces define, by cooperation, a plurality of instantaneous centres of rotation between the elements 10 and 20, all of which are advantageously located in the disk space occupied by the disk 3. The existence of that plurality of instantaneous centres of rotation can, by way of variation, be desirable in some cases of surgical treatment, the surfaces 15 and 25 then having suitable inwardly curved profiles which do not correspond strictly to portions of the sphere S.

Moreover, in the example under consideration in the Figures, the surfaces 15 and 25 of the left-hand elements 10 and 20, on the one hand, and the surfaces 15' and 25' of the right-hand elements 10' and 20', on the other hand, define respective centres of rotation substantially coincident at C. In other words, the surfaces 15' and 25' correspond approximately to portions of the above-mentioned sphere S, as visible in FIG. 2. In a variant not shown, it is possible for the centres of rotation defined respectively by the left-hand elements 10, 20 and the right-hand elements 10', 20' not to be coincident, the kinematics of the guiding then imposed by the device 9 being more complex than that described above since the vertebrae 1 and 2 are displaced one relative to the other in respect of two distinct centres of rotation, at least instantanously. This type of kinematics can be desirable in come cases of surgical treatment of the spine.

In order to limit the amplitude of the relative rotary movements between the vertebral elements 10 and 20, the part 24 is equipped with a pin 26 that is integral with the remainder of that part and projects from the surface 25 in a substantially mediolateral direction directed away from the spine. The pin 26 is received in a through-aperture 16 provided in the lower part 14, which opens medially at the surface 15. The diameter of the pin 26 is slightly smaller than the diameter of the aperture 16, so that the pin is able to move freely therein, in all directions ortho-radial to the sphere S. Rotary movements between the elements 10 and 20, about the point C, are permitted until the pin 26 abuts the wall defining the aperture 16.

In order to strengthen the side-by-side position of the surfaces 15 and 25, a washer 30 is fitted around the free end of the pin 26, in abutment against the convex lateral surface 17 of the part 14. The washer 30 is associated with a locking screw 32 screwed round the threaded free end of the pin 26.

Analogous arrangements, namely a pin 26', an aperture 16', a washer 30' and a screw 32', are provided symmetrically in the region of the vertebral elements 10' and 20'.

Lateral implantation of the device 9 is particularly simple and rapid because only the elements 10, 20, 10' and 20' are to be attached firmly to the vertebrae 1 and 2, by means of the above-mentioned bone anchorage screws. In practice, the elements are placed in position simultaneously, with the lower parts 14 and 14' of the elements 10 and 10' covering laterally the upper parts 24 and 24' of the elements 20 and 20'. In that manner, the surgeon is able to implant the device with the surfaces 15 and 25, on the one hand, and 15' and 25', on the other hand, in contact with one another, for a predetermined extension configuration of the vertebrae. The cooperation of the surfaces 15 and 25 on the left side of the vertebrae and the cooperation of the surfaces 15' and 25' on the right side maintain the longitudinal spacing of the vertebrae 1 and 2, according to direction 4, with a spacing predetermined by the surgeon.

Various arrangements and variants of the device 9 mentioned above are also envisageable:

the structure covering the parts 14 and 24, 14' and 24' can be inverted so that, in a variant not shown, the upper part of each lower vertebral element covers laterally the lower part of each upper vertebral element;

in the exemplary embodiment shown in the figures, the device 9 is implanted in the region of the left and right sides of the vertebrae 1 and 2; by way of variation, the device can comprise only one pair, left or right, of two vertebral elements, in particular for certain specific cases of surgical treatment; and/or the same vertebral element can include both an upper part delimiting a first guide surface of the type of surfaces 14, 24, 14' and 24', which is to rest against an associated surface of a second vertebral element located above the first element, and a lower part delimiting a second guide surface of that type, which is to rest against an associated surface of a third vertebral element located beneath the first element; the corresponding device then extends along three adjacent vertebrae.

The invention claimed is:

1. A device (9) for lateral stabilization of the spine, in use intended to reproduce an articulating intervertebral link joint, said device comprising:

four vertebral elements (10, 20, 10', 20'), i) a left-hand pair of said vertebral elements (10, 20) in use to be attached on a left side of two adjacent vertebrae (1, 2) by bone anchoring screws, ii) a right-hand pair of said vertebral elements (10', 20') in use to be implanted on a right side of the two adjacent vertebrae (1, 2) by the bone anchoring screws, the left-hand pair of said vertebral elements (10, 20) including i) an upper vertebral element (10) in use implanted in a region of an upper one of the two adjacent vertebra (1), and ii) a lower vertebral elements (20) in use implanted in a region of a lower one of the two adjacent vertebra (2), the right-hand pair of said vertebral elements (10', 20') including i) an upper vertebral element (10') in use implanted in a region of an upper one of the two adjacent vertebra (1), and ii) a lower vertebral element (20') in use implanted in a region of a lower one of the two adjacent vertebra (2), the left-hand pair of said vertebral elements (10, 20) and the right-hand pair of said vertebral elements (10', 20'), in use implanted in a symmetrical manner relative to a sagittal plane of the spine, corresponding to a longitudinal direction (4) of the spine, a pair of lower guide elements (24, 24'), one of the lower guide elements integrally connected respectively to each of the left-hand and right-hand lower vertebral elements (20, 20') to define left-hand and right-hand lower bodies (21, 21');

a pair of upper guide elements (14, 14'), one of the upper guide elements integrally connected respectively to each of the left-hand and right-hand upper vertebral elements (10, 10') to define left-hand and right-hand upper bodies (11, 11'), connecting elements (26, 30, 32) arranged so that in use each upper guide element is connected with a corresponding lower guide element, with each upper guide element laterally covering the corresponding lower guide element, so as to extend generally along a same lateral side of the bodies of the vertebrae and to press and slide against surfaces of each other so that these surfaces define a center of rotation (C) located in a intervertebral disc space between the two adjacent vertebrae, the left-hand and right-hand lower bodies (21, 21') and the corresponding left-hand and right-hand upper bodies (11, 11') rotatable relative to the other about the center of rotation (C).

2. The device (9) for lateral stabilization of the spine of claim 1, wherein, each lower guide element and each upper guide element is in a form of a cup, in use, i) a concavity of the cup is turned towards the vertebrae, ii) a principal dimension of each lower guide element and each upper guide element extends substantially parallel to the longitudinal direction (4) of the spine, and iii) in frontal section of a substantially vertical cutting plane parallel to a mediolateral direction, the left-hand upper body (11) has an inverted L cross-section with a rounded main limb facing the spine and the left-hand lower body (21) has a L-shaped cross-section with a rounded main limb facing the spine.

3. The device (9) for lateral stabilization of the spine of claim 2, wherein, in use, a medial face of each upper guide element (14, 14') delimits a concave surface (15), a lateral face of each upper part (24, 24') delimits a convex surface (25) resting and slidable against the concave surface (15) of the upper guide element (14, 14').

4. The device (9) for lateral stabilization of the spine of claim 2, wherein, in use, i) a medial face of each upper guide element (14, 14') delimits a concave surface (15), a lateral face of each upper part (24, 24') delimits a convex surface (25) resting and slidable against the concave surface (15) of the upper guide element (14, 14'), ii) the concave medial face (15) and the convex lateral face (25) being mutually complementary and corresponding approximately to portions of a sphere S having a centre corresponding to the center of rotation (C), and iii) the concave medial face (15) and the convex lateral face (25) rest against one another in a sliding manner and are movable one relative to the other by rotation about the center of rotation (C) in the manner of a ball-and-socket joint with a center at the center of rotation (C).

5. The device (9) for lateral stabilization of the spine of claim 4, wherein, in use, the concave medial face (15) and the convex lateral face (25) cooperate in such a manner as to guide the articulating movements between the vertebrae about the center of rotation (C), the center of rotation (C) being located in the intervertebral disk space, rotary movements imposed by the cooperation of the concave medial face (15) and the convex lateral face (25) providing anatomical intervertebral articulating movements.

6. The device (9) for lateral stabilization of the spine of claim 2, wherein, the connecting elements (26, 30, 32) comprise i) a pin (26, 26') integral with each lower guide element (24, 24') and projecting in a substantially mediolateral direction directed away from the spine, each pin (26) having a threaded free end, ii) a through-aperture (16) provided in each upper guide element (14, 14'), each pin (26) received in a corresponding through-aperture (16), each pin (26) freely movable within the corresponding through-aperture (16), and iii) a locking screw (32) screwed round the threaded free end of each pin (26).

7. The device (9) for lateral stabilization of the spine of claim 2, wherein, a medial face of each upper guide element (14, 14') delimits a concave surface (15), a lateral face of each upper part (24, 24') delimits a convex surface (25) resting and slidable against the concave surface (15) of the upper guide element (14, 14'), the concave surface (15) and the convex surface (25) being guide surfaces and being substantially complementary to one another.

8. The device (9) for lateral stabilization of the spine of claim 7, wherein, each guide surface (15, 25, 15', 25') corresponds substantially to a portion of a sphere (S) having center (C) corresponds to said center of rotation (C).

9. The device (9) for lateral stabilization of the spine of claim 8, wherein, the guide surfaces (15, 25, 15', 25') define a permanent center of rotation (C) when the vertebrae (1, 2) equipped with the four vertebral elements (10, 20, 10', 20') are displaced with respect to each other.

10. The device (9) for lateral stabilization of the spine of claim 1, wherein, the connecting elements (26, 30, 32) comprise i) a pin (26, 26') integral with each lower guide element (24, 24') and projecting in a substantially mediolateral direction directed away from the spine, each pin (26) having a threaded free end, ii) a through-aperture (16) provided in each upper guide element (14, 14'), each pin (26) received in a corresponding through-aperture (16), each pin (26) freely movable within the corresponding through-aperture (16), and iii) a locking screw (32) screwed round the threaded free end of each pin (26).

11. The device (9) for lateral stabilization of the spine of claim 1, wherein, the connecting elements includes parts (16, 26, 16', 26') for limiting an amplitude of relative movements of rotation between the vertebral elements (10, 20, 10', 20').

12. The device (9) for lateral stabilization of the spine of claim 1, wherein, the limiting parts comprise a pin (26, 26') integral with one of the vertebral elements (20, 20') and projecting from the guide surface (25, 25') carried by the one vertebral element, an orifice (16, 16') adapted to receive the pin (26) with sets of travel, said orifice being in another vertebral element (10μ, 10').

13. A device (9) for lateral stabilization of the spine, in use intended to reproduce an articulating intervertebral link joint, said device comprising:

four vertebral elements (10, 20, 10', 20'), i) a left-hand pair of said vertebral elements (10, 20) in use to be attached on a left side of two adjacent vertebrae (1, 2), ii) a right-hand pair of said vertebral elements (10', 20') in use to be implanted on a right side of the two adjacent vertebrae (1, 2), the left-hand pair of said vertebral elements (10, 20) including i) an upper vertebral element (10) in use implanted in a region of an upper one of the two adjacent vertebra (1), and ii) a lower vertebral element (20) in use implanted in a region of a lower one of the two adjacent vertebra (2), the right-hand pair of said vertebral elements (10', 20') including i) an upper vertebral element (10') in use implanted in a region of an upper one of the two adjacent vertebra (1), and ii) a lower vertebral element (20') in use implanted in a region of a lower one of the two adjacent vertebra (2), the left-hand pair of said vertebral elements (10, 20) and the right-hand pair of said vertebral elements (10', 20'), in use implanted in a symmetrical manner relative to a sagittal plane of the spine, corresponding to a longitudinal direction (4) of the spine, a pair of lower guide elements (24, 24'), one of the lower guide elements integrally connected respectively to each of the left-hand and right-hand lower vertebral elements (20, 20') to define left-hand and right-hand lower bodies (21, 21');

a pair of upper guide elements (14, 14'), one of the upper guide elements integrally connected respectively to each of the left-hand and right-hand upper vertebral elements (10, 10') to define left-hand and right-hand upper bodies (11, 11'), connecting elements (26, 30, 32) arranged so that in use each upper guide element is slidably and rotatably connected with a corresponding lower guide element, with each upper guide element and the corresponding lower guide element rotatably about a center of rotation (C) located in a intervertebral disc space between the two adjacent vertebrae.

14. The device (9) for lateral stabilization of the spine of claim 13, wherein,
each lower guide element and each upper guide element is in a form of a cup,
in use, i) a concavity of the cup is turned towards the vertebrae, ii) a principal dimension of each lower guide element and each upper guide element extends substantially parallel to the longitudinal direction (4) of the spine, and iii) in frontal section of a substantially vertical cutting plane parallel to a mediolateral direction, the left-hand upper body (11) has an inverted L cross-section with a rounded main limb facing the spine and the left-hand lower body (21) has a L-shaped cross-section with a rounded main limb facing the spine.

15. The device (9) for lateral stabilization of the spine of claim 14, wherein,
in use, a medial face of each upper guide element (14, 14') delimits a concave surface (15), a lateral face of each upper part (24, 24') delimits a convex surface (25) resting and slidable against the concave surface (15) of the upper guide element (14, 14').

16. The device (9) for lateral stabilization of the spine of claim 14, wherein,
in use, i) a medial face of each upper guide element (14, 14') delimits a concave surface (15), a lateral face of each upper part (24, 24') delimits a convex surface (25) resting and slidable against the concave surface (15) of the upper guide element (14, 14'), ii) the concave medial face (15) and the convex lateral face (25) being mutually complementary and corresponding approximately to portions of a sphere S having a centre corresponding to the center of rotation (C), and iii) the concave medial face (15) and the convex lateral face (25) rest against one another in a sliding manner and are movable one relative to the other by rotation about the center of rotation (C) in the manner of a ball-and-socket joint with a center at the center of rotation (C).

17. The device (9) for lateral stabilization of the spine of claim 16, wherein,
in use, the concave medial face (15) and the convex lateral face (25) cooperate in such a manner as to guide the articulating movements between the vertebrae about the center of rotation (C), the center of rotation (C) being located in the intervertebral disk space, rotary movements imposed by the cooperation of the concave medial face (15) and the convex lateral face (25) providing anatomical intervertebral articulating movements.

18. The device (9) for lateral stabilization of the spine of claim 13, wherein,
the connecting elements (26, 30, 32) comprise i) a pin (26, 26') integral with each lower guide element (24, 24') and projecting in a substantially mediolateral direction directed away from the spine, and ii) a through-aperture (16) provided in each upper guide element (14, 14'), each pin (26) received in a corresponding through-aperture (16), each pin (26) freely movable within the corresponding through-aperture (16).

19. The device (9) for lateral stabilization of the spine of claim 13, wherein,
a medial face of each upper guide element (14, 14') delimits a concave surface (15), a lateral face of each upper part (24, 24') delimits a convex surface (25) resting and slidable against the concave surface (15) of the upper guide element (14, 14'), the concave surface (15) and the convex surface (25) being guide surfaces and being substantially complementary to one another.

20. The device (9) for lateral stabilization of the spine of claim 19, wherein,
each guide surface (15, 25, 15', 25') corresponds substantially to a portion of a sphere (S) having center (C) corresponds to said center of rotation (C).

21. The device (9) for lateral stabilization of the spine of claim 20, wherein,
the guide surfaces (15, 25, 15', 25') define a permanent center of rotation (C) when the vertebrae (1, 2) equipped with the four vertebral elements (10, 20, 10', 20') are displaced with respect to each other.

22. A device (9) for lateral stabilization of the spine, in use intended to reproduce an articulating intervertebral link joint, said device comprising:
a pair of vertebral elements (10, 20, 10', 20'), the pair of said vertebral elements (10, 20) in use to be attached on a side of two adjacent vertebrae (1, 2), the pair of said vertebral elements (10, 20) including
i) an upper vertebral element (10) in use implanted in a region of an upper one of the two adjacent vertebra (1), and ii) a lower vertebral element (20) in use implanted in a region of a lower one of the two adjacent vertebra (2),
the pair of said vertebral elements (10, 20, 10', 20'), in use implanted in a symmetrical manner relative to a sagittal plane of the spine, corresponding to a longitudinal direction (4) of the spine,
a lower guide element (24, 24') integrally connected to the lower vertebral element (20, 20') to define a lower body (21, 21');
an upper guide element (14, 14') integrally connected to the upper vertebral element (10, 10') to define an upper body (11, 11'),
connecting elements (26, 30, 32) arranged so that in use the upper guide element is connected with the lower guide element so as to extend generally along the lateral side of the bodies of the vertebrae and to press and slide against surfaces of each other so that these surfaces define a center of rotation (C) located in a intervertebral disc space between the two adjacent vertebrae, the lower body (21, 21') and the upper body (11, 11') rotatable relative to the other about the center of rotation (C).

23. The device (9) for lateral stabilization of the spine of claim 22, wherein, the lower guide element and the upper guide element are in a form of a cup, in use, i) a concavity of the cup is turned towards the vertebrae, ii) a principal dimension of the lower guide element and the upper guide element extends substantially parallel to the longitudinal direction (4) of the spine, and iii) in frontal section of a substantially vertical cutting plane parallel to a mediolateral direction, the left-hand upper body (11) has an inverted L cross-section with a rounded main limb facing the spine and the lower body (21) has a L-shaped cross-section with a rounded main limb facing the spine.

* * * * *